United States Patent [19]
Ogiri et al.

[11] Patent Number: 5,274,931
[45] Date of Patent: Jan. 4, 1994

[54] ON-LINE MOISTURE CONTROL METHOD FOR POWDERED OR GRANULAR MATERIALS AND A SYSTEM TO EXECUTE THE METHOD

[75] Inventors: Hiroshi Ogiri, Kanagawa; Kazue Murata, Nara; Sadaaki Tanaka, Osaka, all of Japan

[73] Assignee: Kabushiki, Kaisha, Matsui, Seisakusho, Japan

[21] Appl. No.: 887,826

[22] Filed: May 26, 1992

Related U.S. Application Data

[62] Division of Ser. No. 557,865, Jul. 26, 1990, Pat. No. 5,146,692.

[30] Foreign Application Priority Data

Aug. 1, 1989 [JP] Japan .................................. 1-201049

[51] Int. Cl.$^5$ .............................................. F26B 21/06
[52] U.S. Cl. ........................................... 34/46; 34/36; 34/54; 34/89
[58] Field of Search ................... 34/12, 56, 46, 48, 50, 34/54, 89, 19, 168, 44, 36

[56] References Cited

U.S. PATENT DOCUMENTS

| | | | |
|---|---|---|---|
| 4,043,050 | 8/1977 | Hancock | 34/48 |
| 4,575,948 | 3/1986 | Massey et al. | 34/56 |
| 4,578,878 | 4/1986 | Mizuta et al. | 34/48 |
| 4,660,298 | 4/1987 | Nambu et al. | 34/46 |
| 4,750,273 | 6/1988 | Parkes et al. | 34/56 |
| 4,896,795 | 1/1990 | Ediger et al. | 34/56 |
| 4,924,601 | 5/1990 | Bercaw | 34/46 |
| 5,165,180 | 11/1992 | Ogiri et al. | 34/46 |

*Primary Examiner*—Henry A. Bennett
*Assistant Examiner*—Denise L. Gromada
*Attorney, Agent, or Firm*—Jones, Tullar & Cooper

[57] ABSTRACT

An on-line moisture control method for powdered or granular materials and a related system to practice the method. A fixed amount of materials are sampled by a material sampling means, transported into a heat treatment chamber having an airtight heating part, heated in the heat treatment chamber while an inert gas is supplied therein, and the weight measured by a weight measuring unit. The moisture generated by heating the materials is sent to a moisture measuring unit together with the inert gas. An operation unit receives the weight value measured by the weight measuring unit and the titrated value measured by the moisture measuring unit, and calculates the moisture content of the materials and displays the value.

2 Claims, 7 Drawing Sheets

PRIOR ART

ON-LINE MOISTURE CONTROL METHOD FOR POWDERED OR GRANULAR MATERIALS AND A SYSTEM TO EXECUTE THE METHOD

This is a division of co-pending application Ser. No. 07/557,865, filed on Jul. 26, 1990, now U.S. Pat. No. 5,146,692.

BACKGROUND OF THE INVENTION

1. Field of the Invention

The present invention relates to a newly constructed on-line moisture control method wherein powdered or granular materials including inorganic materials such as resin and ceramic are automatically sampled and the moisture content thereof quickly measured and to an on-line moisture control system for performing the method.

2. Prior Art

Generally, keeping the moisture content of resin materials constant in order to maintain good quality of the resin products has created a most important problem because with an inappropriate moisture content of the resin materials to be supplied into a molding machine defects such as a silver line or void are caused. Therefore, resin materials are usually dried by the use of a hopper dryer prior to being supplied into the molding machine.

However, before the resin materials are fed into the hopper dryer they are apt to absorb moisture in the air while stored in a silo or a tank of intermediate stage for a fixed period of time after a kraft bag or a flexible container which is used to carry resin materials is opened. Accordingly a fixed heating temperature and a fixed heating time are set for the hopper dryer which is based on an estimated moisture content of the resin materials. But such a conventional method for drying resin materials by the use of a hopper dryer leaves further room for improvement in saving labor.

On the other hand, a titration analysis using a Karl Fischer reagent has been conventionally known as a method for analyzing and measuring the moisture content of resin materials. A moisture measuring unit has been developed in which a titration analysis by a Karl Fischer reagent is performed by means of a coulometric method, a volumetric method and an absorptive photometric method, whereby a high accuracy can be obtained.

Figure 8:
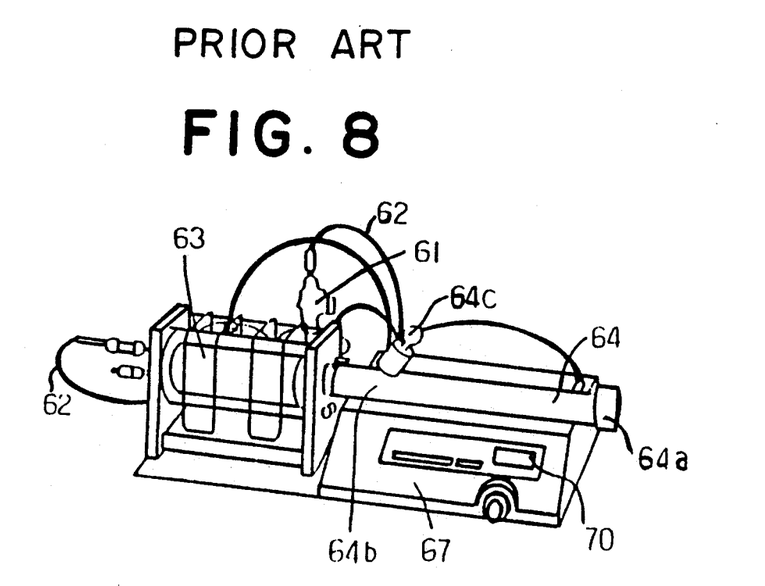
FIG. 8 illustrates the outer appearance of a coulometric moisture measuring unit.
Figure 9:
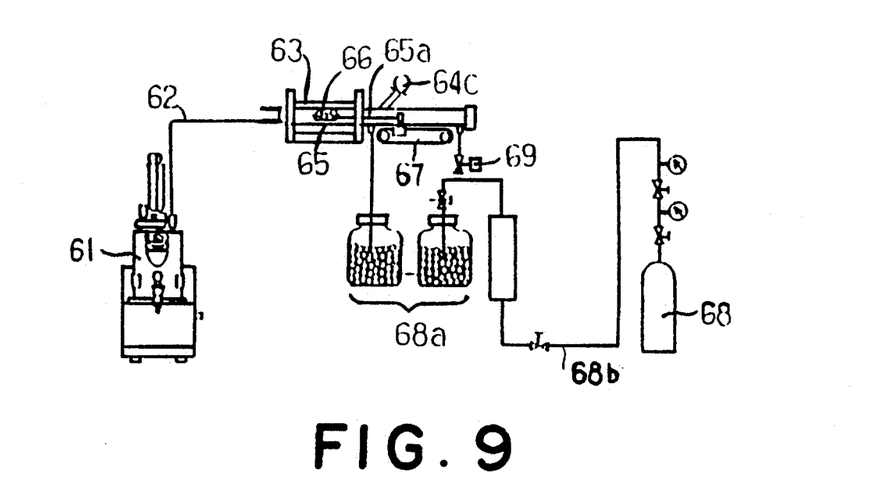
FIG. 9 is a block diagram showing the principle parts of the unit illustrated in FIG. 8.

FIGS. 8 and 9 show the basic construction of a coulometric moisture measuring unit.

This unit is constructed such that a moisture measuring analyzer 61 which performs a coulometric titration by means of a Karl Fischer reagent is connected to a heating chamber 63 to heat samples such as powdered or granular materials. In the chamber 63 connected with the analyzer 61 through a conduit 62, powdered or granular materials 66 put on a boat 65 are transferred and contained by an automatic sample loading unit 67. The moisture produced by heating the materials 66 in the chamber 63 is introduced into the analyzer 61 together with a nitrogen gas fed into the chamber 63, the moisture being titrated and analyzed by a Karl Fischer reagent by the use of coulometric titration. Then the result of the analysis is shown on a display 70.

However, such a moisture analyzer 61 has troublesome problems because the following procedures must be repeated for each sample of the materials.

In order to feed sample materials 66 into the heating chamber 63, the boat 65 is inserted by opening an insert port 64a of an insertion pipe 64 extending from the heating chamber 63 by reducing the caliber and is pushed into a sample feeding portion 64b by means of a rod 65a, the materials 66 sampled by a sampling unit (not illustrated) being loaded on the boat 65 thus contained in the pipe 64 after a cap 64c of the feeding portion 64b is removed.

In this case, a feeding machine (not illustrated) which contains sample materials 66 is mated with the cap 64c so that the opening of the feeding machine fits the opening of the cap 64c. After a purge valve 69 is opened to atmosphere, a dried pressurized nitrogen gas supplied through a feed pipe 68b and a drying chamber 68a from a gas cylinder 68 is replaced and discharged in order to prevent outside air from entering into the heating chamber 63.

Further, after completion of the heat treatment, the materials 66 loaded on the boat 65 are transferred by the automatic loading unit 67 into the insert port 64a or the insertion pipe 64 to be discharged.

According to the above-mentioned troublesome problems, as a rule, such a moisture measuring analyzer has been used for quality inspection at a laboratory by a professional inspector. It is hardly possible to sample powdered or granular materials one after another and measure the moisture content thereof at a molding site.

SUMMARY OF THE INVENTION

An object of the present invention is to provide an on-line moisture control method wherein a fixed amount of powdered or granular materials is automatically sampled and fed into a dried heat treatment chamber required for measuring the moisture content of the materials and being heated therein, and to provide an on-line moisture control system by using the method.

A further object of the invention is to provide an initial moisture control for powdered or granular materials before being dried (usually controlled by a lot) and a moisture control of the materials which have been dried by a hopper dryer and the like quickly and accurately while saving labor, by conducting an automatic sampling of the materials and an accurate and swift measurement of the moisture content at the site.

An on-line moisture control method according to the present invention is characterized by repeat the following steps each time materials are sampled; transporting the sampled and weighed materials are into a heat treatment chamber having an airtight heating means, heating the materials in the chamber while a pressurized and dried inert gas is fed therein; and supplying the moisture produced from the materials into a moisture measuring unit together with the inert gas. Such an on-line method is roughly divided into two methods; the materials are transported by the use of a mechanical material transporting means, and the materials are transported by a transport gas, such as air or an inert gas.

This invention uses a moisture measuring unit which performs a coulometric titration, a volumetric titration or a simple absorptive photometric titration which has been disclosed in Japanese Patent Application 63-039291, A Karl Fischer reagent being used for all these methods.

To perform the method according to the present invention, an on-line moisture control system including a material sampling means having a measuring device to supply materials into a heat treatment chamber is proposed. And a system including a material measuring chamber having a weight detection sensor above the heat treatment chamber instead of providing the measuring device to the material sampling means is also proposed. Further, an on-line moisture control system wherein a fixed amount of materials is transferred by a pneumatic transporting means into a material measuring chamber by the use of a material suction unit. The material suction unit has a nozzle constructed such that an injection port of pressurized gas is disposed at an initial end side of a material suction port formed at the lateral leading portion of a transport pipe of the transporting means so as to be opposite to the transporting destination of the materials.

By the present invention materials are heated in a heat treatment chamber by heating means such as a heater, and the on-line moisture control system which is more appropriate for saving energy by utilizes the retained heat of the materials which have been heated in the heat chamber.

According to the system of the present invention, the analyzed value obtained by a moisture measuring unit which performs titration and analysis by the use of a titration reagent such as a Karl Fischer reagent and the weight of sampled materials before heat treatment or after heat treatment are sent to an operation unit to be calculated, whereby an accurate moisture content can be obtained quickly. For this purpose, a weight measuring unit for the materials before they are heated and for the materials after they are heated are proposed.

Also according to the system of the present invention, a dried inert gas is required to be introduced (or replaced) into a heat treatment chamber when powdered or granular materials are supplied into the chamber and the supplied materials are heated for moisture analysis. In this case a gas feeding means which can supply an inert gas through a control damper provided under the heat treatment chamber or a second control damper under a material storing chamber is simultaneously proposed.

Therefore, the system of the present invention simultaneously proposed with the present method is characterized as follows.

A first system of the present invention comprises a material sampling means having a measuring device to sample a fixed amount of powdered or granular materials, a heat treatment chamber with an airtight heating means having enough capacity to contain the materials sampled by the sampling means, a transport pipe provided between the sampling means and the heat chamber and having a control valve which controls the supply of materials from the sampling means and a gas vent valve to open to atmosphere, a moisture measuring unit led from the upper part of the heat chamber by a branch pipe having a control valve, a control damper provided under the heat chamber to discharge the materials stored in the heat chamber, an inert gas feeding means having a fed port at the lower part of the heat chamber and a feed pipe interposed by a control valve which controls the introduction of pressurized and dried inert gas into the heat chamber, a weight measuring unit provided under the damper, and an operation unit which receives the measured weight value of of materials from the weight measuring unit and the titrated and analyzed value from the moisture measuring unit, thereby calculating the moisture content of sampled fixed amounts of materials and displaying and outputting the obtained value.

A second system of the present invention comprises a material sampling means having a measuring device to sample a fixed amount of powdered or granular material, an airtight weight measuring station having a vent valve to open to atmosphere and including a weight measuring unit to measure the weight of the materials supplied by the sampling means and a hopper to receive the materials measured at the weight measuring unit, a heat treatment chamber with an airtight heating means having enough capacity to contain the materials sampled by the sampling means, a transport pipe provided between the weight measuring station and the heat treatment chamber and having a control valve to control the supply of materials from the hopper, a moisture measuring unit led from the upper part of the heat chamber by a branch pipe having a control valve, a control damper provided under the heat chamber to discharge the materials stored in the heat chamber, an inert gas feeding means having a feed port at the lower part of the heat chamber and a control valve to control the introduction of inert gas into the heat chamber, and an operation unit which receives the measured weight value of the materials from the weight measuring unit and the titrated and analyzed value from the moisture measuring unit, thereby calculating the moisture content of sampled fixed amounts of materials and displaying and outputting the obtained value.

A third system of the present invention comprises a material supply means to supply powdered or granular materials, a material measuring chamber which is provided with a weight detection sensor to measure a fixed amount of materials supplied from the supply means and stores the weighed materials, a transport pipe having a control valve the opening and closing operations of which are controlled by the sensor and a vent valve to open to atmosphere and connecting the measuring chamber and the supply means, a heat treatment chamber with an airtight heating means having enough capacity to contain all the materials stored in the measuring chamber and connected under the measuring chamber through a first control damper, a moisture measuring unit led from the upper part of the heat chamber by a branch pipe having a control valve, a second control damper provided under the heat chamber to discharge the materials stored in the heat chamber, an inert gas feeding means having a feed port at the lower part of the heat chamber and a feed pipe interposed by a control valve which controls the introduction of pressurized and dried inert gas into the heat chamber, a weight measuring unit provided under the second damper, and an operation unit which receives the measured weight value of materials from the weight measuring unit and the titrated and analyzed value from the moisture measuring unit, thereby calculating the moisture content of sampled fixed amounts of materials and displaying and outputting the obtained value.

A fourth system of the present invention comprises a material suction unit having a nozzle constructed such that an injection port of pressurized gas is disposed at an initial end side of a material suction port formed at the lateral leading portion of a transport pipe so as to be opposite to the transporting destination of the materials, the nozzle being inserted into a bed of materials to draw the materials in, a material measuring chamber connected to the suction unit by a transport pipe line having a control valve, provided with a filtering device to separate the materials pneumatically transported by the suction unit from the pressurized gas and with a weight detection sensor, a heat treatment chamber with an airtight heating means having enough capacity to contain the materials stored in the measuring chamber and connected under the measuring chamber through a first control damper, a moisture measuring unit led from the upper part of the heat chamber by a branch pipe having a control valve, a second control damper provided under the heat chamber to discharge the materials stored in the heat chamber, an inert gas feeding means having a feed port at the lower part of the heat chamber and a feed pipe interposed by a control valve which controls the introduction of pressurized and dried inert gas into the heat chamber, a weight measuring unit provided under the second damper, and an operation unit which receives the measured weight value of materials from the weight measuring unit and the titrated and analyzed value from the moisture measuring unit, thereby calculating the moisture content of sampled fixed amounts of materials and displaying and outputting the obtained value.

Another system of the present invention is constructed such that a material storing chamber which stores powdered or granular materials heated in the heat treatment chamber in order to apply a retained heat to the heat chamber is provided under the heat chamber, a control damper to discharge the materials stored in the storing chamber is provided under the storing chamber and further a feed pipe having a control valve and extended from an inert gas feeding means is provided at the lower part of the storing chamber.

Still another system of the present invention is constructed such that a material storing chamber which stores powdered or granular materials heated in the heat treatment chamber in order to apply a retained heat to the heat chamber is provided under the heat treatment chamber, a second control damper to discharge the materials stored in the storing chamber is provided under the storing chamber and further a feed pipe having a control valve extended from an inert gas feeding means is provided at the lower part of the storing chamber.

According to a system of the present invention, a gas introduction port having a breathable material is provided at the control damper instead of providing the inert gas feeding means, the port being connected with a feed pipe leading from an inert gas source through a control valve which controls the supply of pressurized and dried inert gas.

According to a system of the present invention, a gas introduction port having a breathable material is provided with the second control damper instead of providing the inert gas feeding means, the port being connected with a feed pipe leading from an inert gas source through a control valve which controls the supply of pressurized and dried inert gas.

According to a system of the present invention, the material storing chamber disposed under the heat treatment chamber to apply a retained heat of materials is provided with a weight detection sensor, the sensor controlling the operations of the control damper or the second control damper to discharge accurately the heated powdered or granular materials sampled at one time and stored in the storing chamber.

According to a system of the present invention, the apparent specific weight of the sampled powdered or granular materials and the volume of the sampled materials are input into the operation unit instead of providing a weight measuring unit, so that a more simplified on-line moisture control system can be achieved by removing the weight measuring unit.

Other features and advantages of the invention will be apparent from the following description taken in connection with the accompanying drawings.

DETAILED DESCRIPTION OF THE PREFERRED EMBODIMENT

Now more detailed descriptions will be given referring to the drawings.

Figure 1:
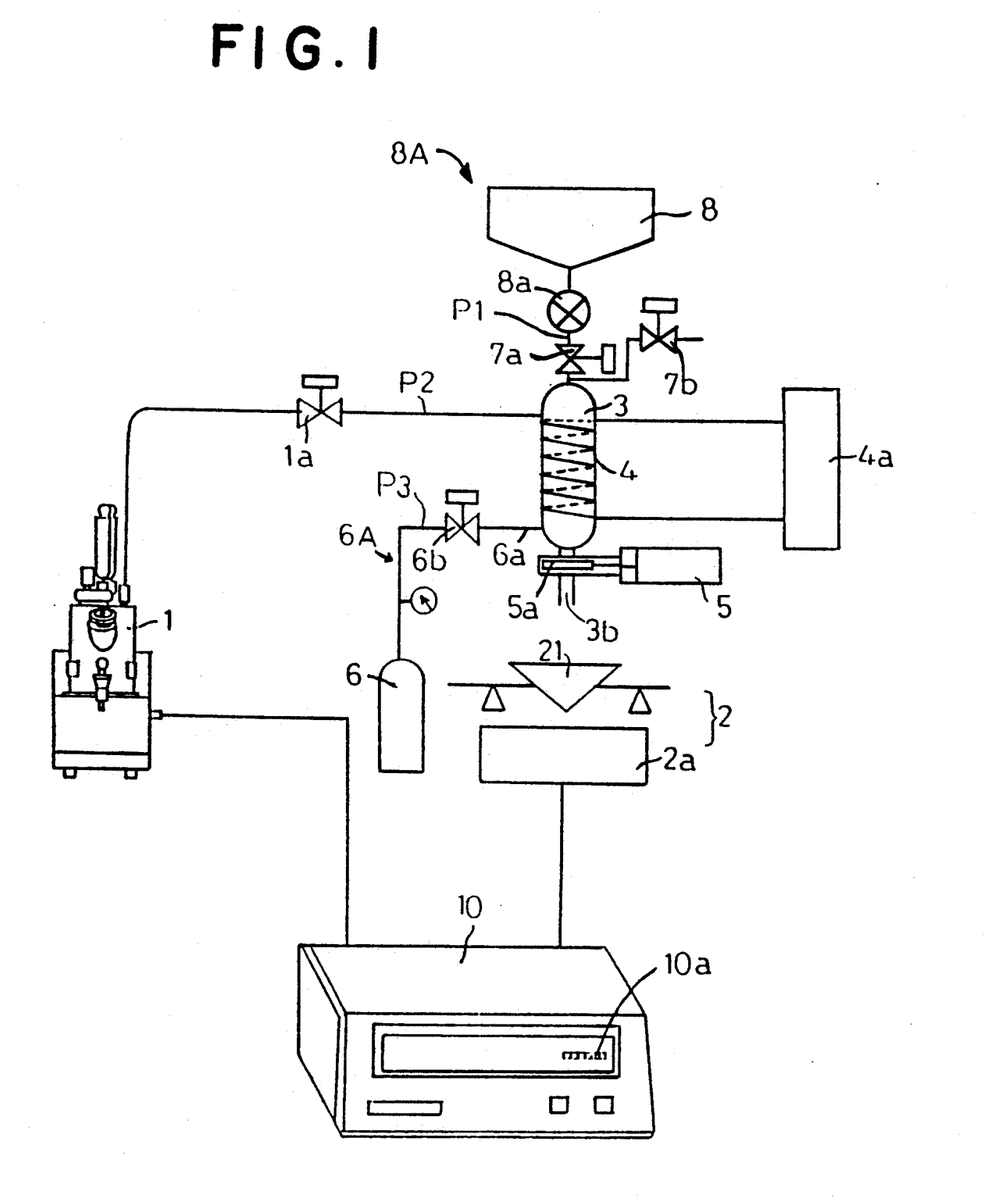
FIG. 1 is a schematic diagram showing a first system according to the present invention.

FIG. 1 shows a schematic diagram of a first system according to the present invention.

In this system a heat treatment chamber 3 made of a heat-resistant glass provided with heating means 4 at its periphery is disposed under a material sampling means 8A. The material sampling means 8A includes a hopper 8 to store powdered or granular materials and a rotary valve 8a thereunder. The sampling means 8A and the heat chamber 3 are connected by a transport pipe P1 having a control valve 7a to control the material supply and a vent valve 7b to open to atmosphere, the valve 7a including a highly airtight valve disc to prevent the leakage of moisture produced when materials are heated in the chamber 3.

A material discharge port 3b provided under the chamber 3 is provided with a solenoid-operated control damper 5 which opens and closes the port 3b by reciprocating a valve disc 5a and a weight measuring unit 2 is provided under the damper 5.

The weight measuring unit 2 is equipped with a receiver 21 which can be opened and closed to receive the heated materials discharged from the port 3b of the heat chamber 3. When the materials are received in the receiver 21, the weight is automatically measured and is converted into an electrical signal at a signal processor 2a of the measuring unit 2, the thus converted data being sent to an operation unit 10.

The heat treatment chamber 3 has enough capacity to contain one sample of powdered or granular material passed by the rotary valve 8a the upper part of the chamber 3 is connected with a branch pipe P2 having a control valve 1a and leading to a moisture measuring unit 1.

Many kinds of trace moisture are measured by measuring unit by means of a Karl Fischer reagent of which an introduction port can be directly connected with the moisture measuring unit 1 by the branch pipe P2. If such a unit is provided, a highly accurate coulometric or volumetric moisture measurement utilizing a Karl Fischer reagent can be achieved by supplying the moisture evaporated by heating materials into the unit 1 together with an inert gas and by inputting the weight of the materials before heated.

The value titrated and analyzed by the moisture measuring unit 1 is converted into an electrical signal and sent to the operation unit 10, like the weight value measured by the weight measuring unit 2. Thus the titrated and analyzed value and the weight value are input into the operation unit 10, the moisture content being calculated, shown on a display 10a and printed out when required.

An inert gas feed port 6a is provided at the lower part of the heat chamber 3 the feed port 6a is connected through a control valve 6b to a gas source 6, which feeds an inert gas such as a dried nitrogen gas or helium gas.

The heat treatment chamber 3 is equipped with a heating means 4 at its periphery constructed by Nesa electrodes or a well-known Nichrome wire. If the heating means 4 is constructed with Nesa electrodes, the materials in the heat chamber 3 can be seen, and also the body of the chamber 3 can be made thin and compact.

The heat treatment chamber 3 is heated to and maintained at a temperature just before the stored materials are vaporized in order to evaporate all the moisture contained in the materials. For this purpose, a temperature control unit 4a establishes and controls the most appropriate temperature of the chamber 3 depending on the materials to be heated therein and before the materials are received therein.

According to this system, when sampling is required, the damper 5 is shut and the control valve 1a is closed to close the branch pipe P2 leading to the moisture measuring unit 1. At the same time the control vale 7a and the vent valve 7b are opened and the rotary valve 8a is driven to rotate while an inert gas is introduced into the chamber 3 by opening the control valve 6b, then samples are supplied into the chamber 3. At this time the vent valve 7b is opened to atmosphere to prevent open air from entering into the chamber 3 when the inert gas is supplied into the chamber 3.

After a fixed amount of powdered or granular material is thus contained in the chamber 3, the control valve 7a and the vent valve 7b are closed with the damper 5 still closed. And the control valve 1a is opened to open the branch pipe P2 leading to the moisture measuring unit 1 while the control valve 6b is opened to introduce an inert gas from the lower part of chamber 3 into and all over the inside thereof.

Under these conditions, the materials are heated in the chamber 3 and the moisture produced by the evaporation of heated materials is supplied into the moisture measuring unit 1 together with the introduced inert gas.

The supply of inert gas continues until the measuring unit 1 detects the end of titration. When the unit 1 detects this end, the display 10a of operation unit 10 shows a sign indicating the end of titration.

After the heat treatment of the powdered or granular materials is thus finished, the materials in the chamber 3 are supplied into the weight measuring unit 2 by opening the damper 5. In the unit 2 materials received at the receiver 21 are weighed and the value is converted into an electrical signal by the signal processor 2a then sent to the operation unit 10, wherein data sent from the moisture measuring unit 1 and the weight measuring unit 2 are calculated and the obtained moisture content of the materials is shown on the display 10a.

Figure 2:
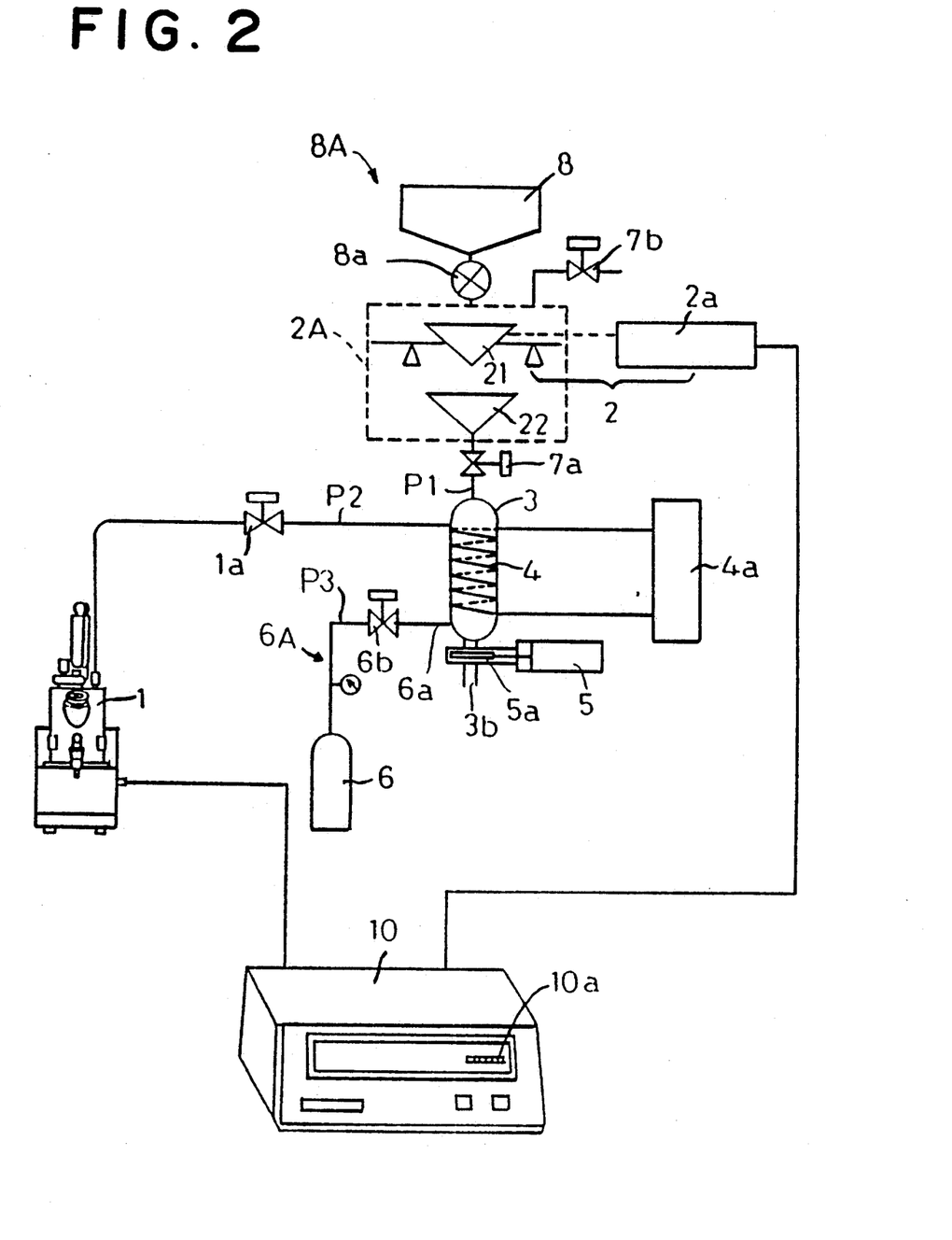
FIG. 2 is a schematic diagram showing a second system according to the present invention.

FIG. 2 shows a schematic diagram of a second system of the present invention.

A weight measuring station 2A FIG. 2 which is airtight and closed for open air is disposed under a material sampling means 8A constructed such that a rotary valve 8a to sample a fixed amount of powdered or granular materials is provided as a measuring device under a hopper 8 which stores the materials. The weight measuring station 2A is comprised of a weight measuring unit 2 having a receiver 21 to receive the materials and a supplementary hopper 22 to receive the materials weighed by the unit 2, and is provided with a vent valve 7b to open to atmosphere.

A heat treatment chamber 3 with an airtight heating means 4 having enough capacity to contain a fixed amount of materials weighed by the rotary valve 8a is disposed under the measuring station 2A. A branch pipe P2 having a control valve 1a and leading to a moisture measuring unit 1 is provided at the upper part of the heat chamber 3 and a feed port 6a of an inert gas feeding means 6A having a control valve 6b to control the introduction of a pressurized and dried inert gas into the chamber 3 is provided at the lower part of the chamber 3.

A control damper 5 to discharge materials is disposed under the chamber 3. The weight value of sampled materials measured by the weight measuring unit 2 and the value titrated and analyzed by the moisture measuring unit 1 are converted into electrical signals respectively and sent to an operation unit 10, as described in the first system.

According to this system, when sampling is required, the damper 5 is shut and the control valve 1a is closed to close the branch pipe P2 leading to the moisture measuring unit 1. At the same time a control vale 7a and the vent valve 7b are opened and the rotary valve 8a is driven to rotate while an inert gas is introduced into the chamber 3 by opening the control valve 6b, resulting in samples being supplied into the weight measuring station 2A. At this time the vent valve 7b is opened to atmosphere.

In the weight measuring station 2A a fixed amount of materials supplied by the rotary valve 8a has fallen into the receiver 21 of the weight measuring unit 2 and received therein, and then measured. Next, the materials are discharged into the supplementary hopper 22, falling by gravity into the heat chamber 3 through a transport pipe P1 and heated therein.

In this system, the vent valve 7b for opening to atmosphere equipped with the weight measuring station 2A is opened when an inert gas is fed into the station 2A through the heat chamber 3 at the same time materials are supplied into the station 2A, whereby the weight of materials is measured under closed and dried circumstances.

After a fixed amount of material is thus supplied into the heat chamber 3, the control valve 7a and the vent valve 7b are closed with the control damper 5 still closed and an inert gas is introduced into the chamber 3 with the control valves 6b and 1a open, thus the moisture evaporated from the heated materials being sent to the moisture measuring unit 1, as described in the first system.

The supply of inert gas continues until the measuring unit 1 detects the end of titration. When the unit 1 detects this end, a display 10a of operation unit 10 shows a sign indicating the end of titration. After the heat treatment of powdered or granular materials is thus finished, the materials are discharged by opening the control damper 5.

Like the first system of the present invention, the operation unit 10 calculates data sent from the moisture measuring unit 1 and the weight measuring unit 2 and shows the obtained moisture content of materials on its display 10a.

Figure 3:
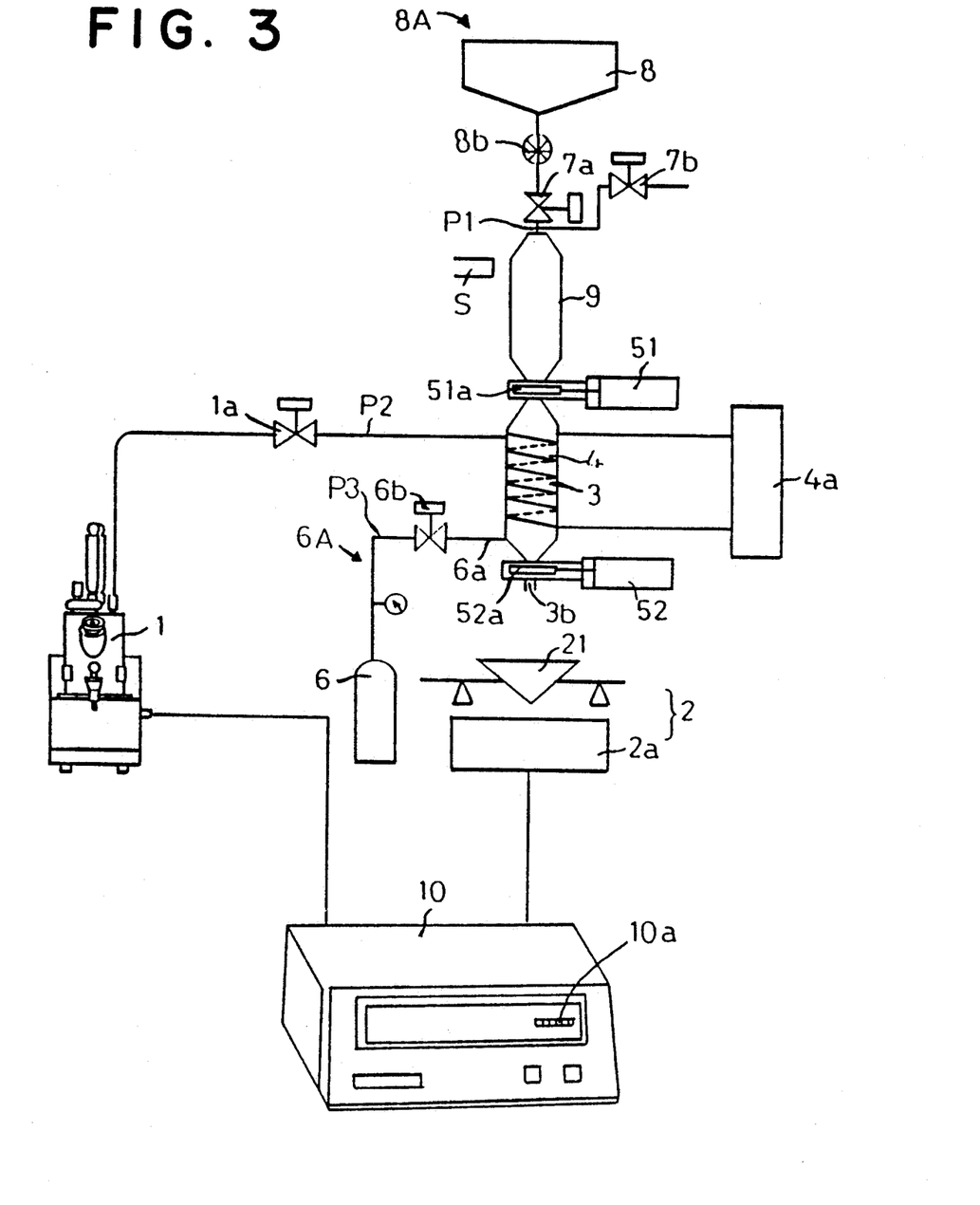
FIG. 3 is a schematic diagram showing a third system according to the present invention.

FIG. 3 is a schematic diagram showing a third system of the present invention.

In this system a rotary valve 8b provided in a material supply means 8A to transport powdered or granular materials doesn't work as a measuring device. A fixed amount of powdered or granular materials is weighed by a material measuring chamber 9 having a weight detection sensor S to detect the level of materials and provided between the material supply means 8A and a heat treatment chamber 3.

Materials are supplied into the material measuring chamber 9 by opening a control valve 7a until the sensor S detects that the supplied materials reach a predetermined level. After a fixed amount of the materials is stored in the chamber 9, the stored materials are supplied into the heat chamber 3 by opening a first control damper 51 provided between the measuring chamber 9 and the heat chamber 3.

A second control damper 52 to discharge the heated materials and a weight measuring unit 2 are provided under the heat treatment chamber 3, with the materials being heated to be titrated and analyzed and weighed by the measuring unit 2.

An operation unit 10 calculates data sent from a moisture measuring unit 1 and the weight measuring unit 2 and indicates the obtained moisture content of the materials on its display 10a. The remaining structure is the same as the above-mentioned first system.

Figure 4:
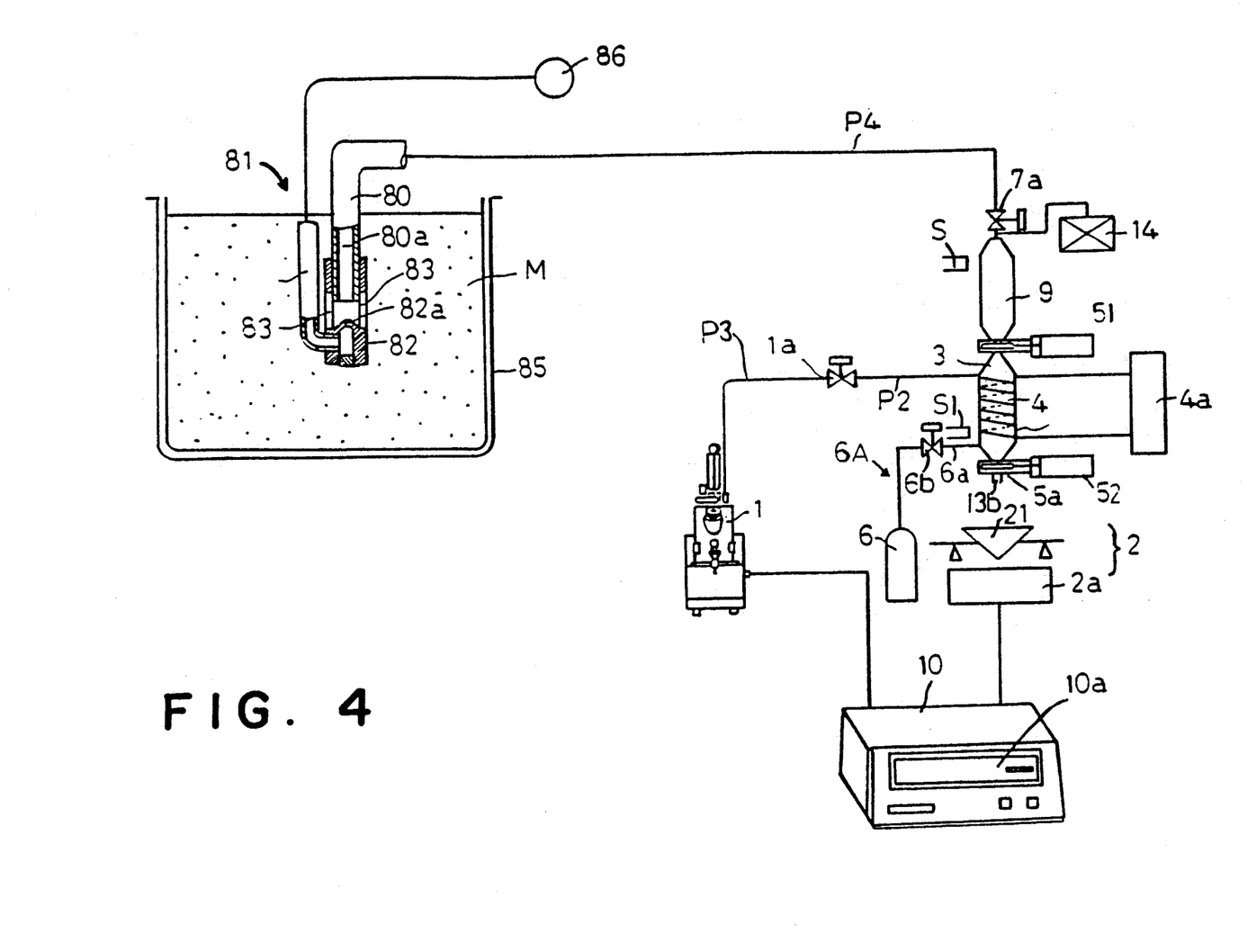
FIG. 4 is a schematic diagram showing a fourth system according to the present invention.

FIG. 4 is a schematic diagram of a fourth system of the present invention.

This system is characterized in that powdered or granular materials are supplied through a transport pipe line P4 by pneumatic transportation by the use of a specially constructed material suction unit 81 which will be described hereinafter. The materials pneumatically transported by the unit 81 are separated from the gas by a filtering device 14 provided at the entrance of the material measuring chamber 9.

A capacitance level sensor S is provided with the chamber 9 as a weight detection sensor, controlling opening and closing operations of a control valve 7a to store a fixed amount of materials in the chamber 9.

The materials stored in the chamber 9 fall into a heat treatment chamber 3 by opening a first control damper 51 and are stored therein. At this time an inert gas introduced from a feed port 6a provided at the lower part of the heat chamber 3 is bled to atmosphere from the filtering device 14 passing through the heat chamber 3 and the measuring chamber 9. Therefore, outside air is prevented from entering both chambers 3 and 9 and these chambers can be kept under dried circumstances which are suitable for measuring and analyzing moisture content.

The material suction unit 81 according to this system is constructed such that a pressurized gas injection port 82a of a nozzle 82 is provided at the initial end side of a material suction port 83 formed at the lateral leading portion of the transport pipe 80 so as to be opposite to the transporting destination of the materials. The suction port 83 of the unit 81 is inserted into a bed of powdered or granular materials M in a tank 85, materials being suck in by injecting a pressurized gas from the nozzle 82 by operating a pressurized gas source 86.

Such a material suction unit 81 has already been disclosed in Japan by the present applicant. Materials are sucked into the pipe 80 when a pressurized gas injected from the port 82a creates a negative pressure at the suction port 83 by the effect of ejection, being transported under pressure by the pressurized gas injected from the nozzle 82. The nozzle 82 is free from clogging caused at the beginning of a suction operation because the apparent area of the suction port becomes larger than that of a conventional suction nozzle having the same caliber. Therefore, this system is preferable to execute an on-line pneumatic transportation of a small amount of materials by the use of a thin transport pipe.

Figure 4A:
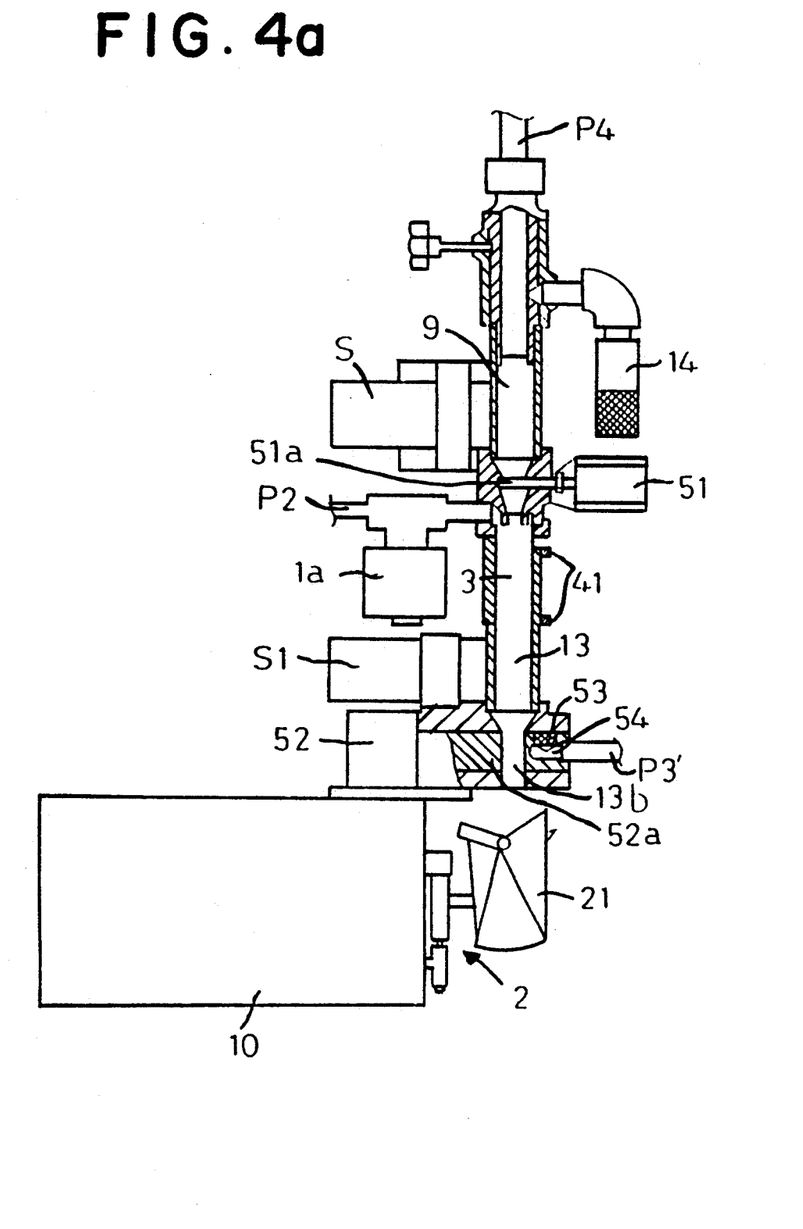
FIG. 4a is an enlarged sectional view of the main part of another preferable embodiment according to the present invention.

FIG. 4a is an enlarged sectional view of the main part of another preferable embodiment according to the present invention.

In the figure, this system includes a heat treatment chamber 3 having a heating means 4 constructed by winding Nichrome wire under the material measuring chamber 9. A first control damper 51, a material storing chamber 13, described hereinafter, provided under the heat chamber 3, a second control damper 52 under the chamber 13, and a weight measuring unit 2 having a receiver 21 to receive powdered or granular materials discharged from a material discharge port 13b of the storing chamber 13 under the damper 52 are interposed under the measuring chamber 9.

Capacitance level sensors S and S1 are provided for the measuring chamber 9 and the storing chamber 13, respectively, as weight detection sensor. A transport pipe line P4 connected with the suction unit (see FIG. 4) at its upstream end is connected with the upper end of measuring chamber 9 and a filtering unit 14 is provided at the side of the chamber 9 to separate the transported materials from a pressurized gas.

The fist control damper 51 provided between the measuring chamber 9 and the heat chamber 3 includes a solenoid-operated highly airtight valve disc 51a. The solenoid-operated second control damper 52 disposed under the storing chamber 13 is constructed so as to be able to introduce an inert gas by filling a breathable ceramic material 53 in a gas introduction pipe 54 even if a valve disc 52a is closed, as described hereinafter. In the figure, the number 1a indicates a control valve interposed in a branch pipe P2 leading to a moisture measuring unit (shown as the numeral 1 in FIG. 4) from the upper part of heat treatment chamber 3.

Figure 5:
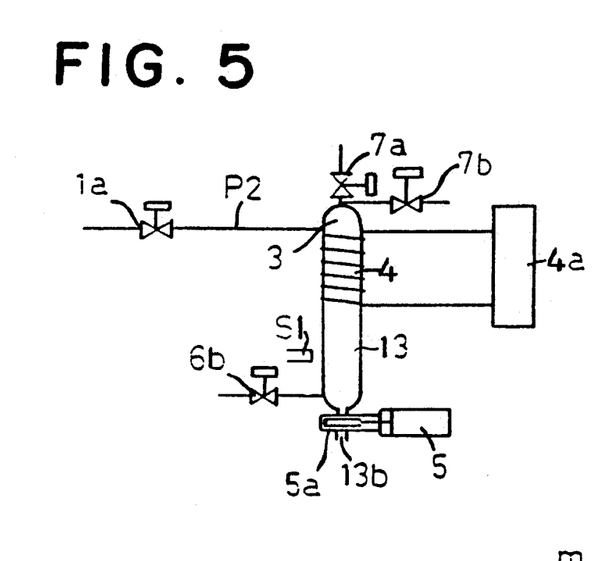
FIGS. 5 and 6 are schematic diagrams of a material storing chamber of other preferable embodiments according to the present invention.

FIG. 5 shows another construction of a material storing chamber according to the systems of the present invention.

In FIG. 5 a material storing chamber 13 to store at least more than one sample of material is provided under a heat treatment chamber 3. A layer of powdered or granular materials to be heated is piled on a layer of materials stored in the storing chamber 13 and heated in the chamber 3.

After the materials of the upper layer are heated in the chamber 3, the materials in the storing chamber 13 are discharged by gravity when a valve disc 5a of control damper 5 is opened. A level sensor S1 is provided with the storing chamber 13 in order to control the amount of discharge, whereby immediately after one sample of the materials is discharged, the valve disc 5a of damper 5 is closed, control valves 7a and 6b are opened and an inert gas is introduced into the chamber 13. At the same time a fixed amount of newly sampled materials is supplied into the heat treatment chamber 3 by a material supply means (not illustrated).

According to this system in which the material storing chamber 13 is provided under the heat treatment chamber 3, powdered or granular materials which have been already heated are stored in the storing chamber 13. Therefore, the chamber 3 is prevented from losing the heat by the supply of materials. In contrast the heat retained by the materials can be applied to the above layer of materials, whereby an energy-saving system and quick analysis can be achieved.

Further according to this system, an inert gas is introduced into the heat chamber 3 by opening the control valve 6b when a new sample of materials is supplied. So, this system is more effective to maintain the temperature in the heat chamber 3 uniform because the inert gas works as a medium to transfer the heat of the materials which already have been heated while the gas maintains the temperature in the chamber 3.

Furthermore according to this system, the weight of the materials may be measured before heating by sampling a fixed amount of materials and feeding it through the chamber 3 without executing heat treatment into the weight measuring unit 2. In this case, as the weight of measured materials at the measuring unit 2 differs from that of the heated materials, the average weight of a few samples which are not heated may be used as the weight data in order to consider the difference between both weights.

Figure 6:
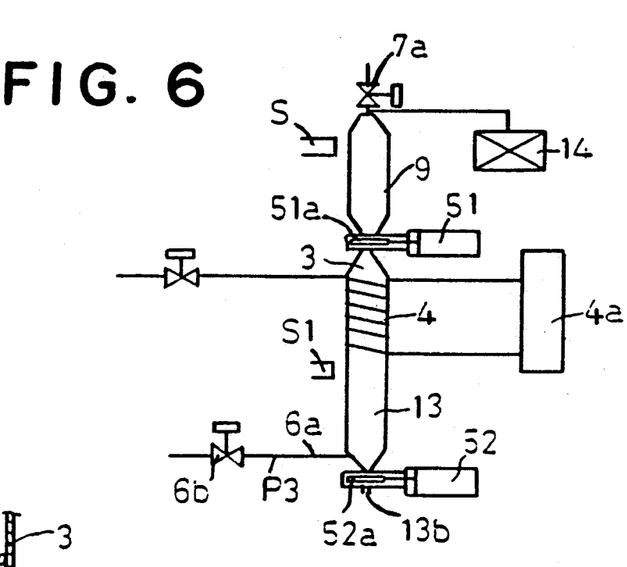

FIG. 6 shows still another construction of the material storing chamber according to the prevent invention preferably used in order to pneumatically transport sampled materials. This system also includes a material storing chamber 13 to store at least more than one sample of materials provided under a heat treatment chamber 3.

A layer of materials to be heated is piled on a layer of materials stored in the storing chamber 13 and heated in the heat chamber 3. After the heat treatment, the materials in the storing chamber 13 fall by gravity and are discharged by opening a valve disc 52a of a second control damper 52. In order to control the discharging amount of materials, a level sensor S1 is provided with the storing chamber 13 as a weight detection sensor, whereby immediately after one sample of materials is discharged, the valve disc 52a is closed, control valves 7a and 6b are opened and an inert gas is introduced into the chamber 13. At this time a fixed amount of materials is supplied into the heat chamber 3 from the material measuring chamber 9 having a weight detection sensor S by opening a valve disc 51a of a first control damper 51. The effect of retained heat of the materials in the storing chamber 13 is the same as the system shown in FIG. 5.

Figure 7:
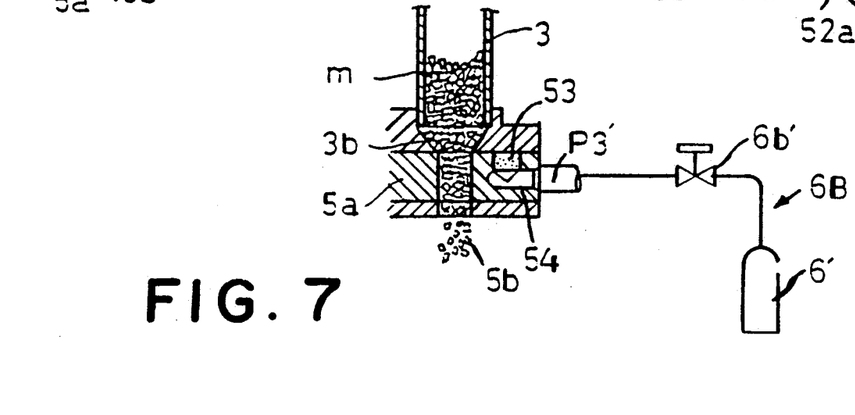
FIG. 7 shows another preferable embodiment of a control damper according to the present invention.

FIG. 7 shows the construction of another embodiment of a control damper provided under a heat treatment chamber 3.

A valve disc 5a of control damper 5 is provided with a valve port 5b to discharge materials. The valve disc 5a has a chamber filled with a breathable ceramic material 53 so as to close a material discharge port 3b constructed under the heat chamber 3 when the valve disc 5a is at its closed position. A gas introduction pipe 54 with one opened end is provided with the ceramic material 53 and the opening of the introduction pipe 54 is connected with a gas feed pipe P3' leading to a pressurized and dried inert gas source 6'.

According to such a construction, as the valve port 5b conforms to the discharge port 3b when the damper 5 is opened, powdered or granular materials m contained in the chamber 3 are discharged by gravity through the port 3b as shown in FIG. 7. When the damper 5 is closed, the ceramic material 53 closes the port 3b and prevents discharge of the materials m. However, an inert gas fed from the introduction pipe 54 successively goes into the heat chamber 3 because the gas can pass through the ceramic material 53, thus the replacement by an inert gas, and the supply of an inert gas when the materials are heated, as described heretofore, can be achieved.

FIG. 7 shows only an embodiment of the damper 5 provided at the discharge port 3b of the heat treatment chamber 3, but in the case that a material storing chamber 13 is further provided, a second control damper 52 provided at the material discharge port 13b of material storing chamber 13 may be similarly constructed.

In the above-mentioned embodiments sampled materials are weighed before being heated or after being heated by a weight measuring unit. However, such a weight measuring unit is removed and the apparent specific weight and the volume of sampled materials may be input into an operation unit. Such a system can further simplify the construction thereof because of the removal of the weight measuring unit, and is more effectively used for the moisture control of the same kind of powdered or granular materials.

In this case, the system may preferably be constructed such that the volume of sampled materials is input into the operation unit 10 automatically.

According to an on-line moisture control method of the present invention, a fixed amount of powdered or granular materials is sampled automatically, supplied into an airtight and dried heat treatment chamber and heated therein while an inert gas is introduced, thus the moisture content of the material is measured.

Further according to a simultaneously proposed on-line moisture control system of the present invention, the following functions can be obtained.

In the system comprising: a material sampling means having a measuring device to sample a fixed amount of powdered or granular materials; a heat treatment chamber with an airtight heating means having enough capacity to contain the materials sampled by the sampling means; a transport pipe provided between the sampling means and the heat chamber, the pipe having a control valve to control the supply of materials from the sampling means and having a gas vent valve to open to atmosphere; a moisture measuring unit led from the upper part of the heat chamber by a branch pipe having a control valve; a control clamper provided under the heat chamber to discharge the materials stored in the heat chamber; an inert gas feeding means having a feed port at the lower part of the heat chamber and having a feed pipe interposed by a control valve to control the introduction of pressurized and dried inert gas into the heat chamber; a weight measuring unit provided under the clamper; and an operation unit which receives the measured weight value of materials from the weight measuring unit and the titrated and analyzed value from the moisture measuring unit, thereby the operation unit calculating the moisture content of a sampled fixed amount of materials and displaying and outputting the calculated value, a fixed amount of powdered or granular materials is sampled by the use of material sampling means provided with a measuring device, the sampled materials are fed into a heat treatment chamber by gravity while an inert gas is introduced, the moisture evaporated from the heated materials is sent to a moisture measuring unit together with the introduced inert gas and the moisture is titrated and analyzed. The materials heated in the heat chamber are fed into a weight measuring unit by opening a control damper. An operation unit receives the value titrated and analyzed by the moisture measuring unit and the weight value measured by the weight measuring unit to calculate the moisture content of materials and displays and outputs the calculated value.

In the system comprising: a material sampling means having a measuring device to sample a fixed amount of powdered or granular materials; an airtight weight measuring station having a vent valve to open to atmosphere, the station including a weight measuring unit to measure the weight of the materials supplied by the sampling means and a hopper to receive the materials measured by the weight measuring unit; a heat treatment chamber with an airtight heating means having enough capacity to contain the materials sampled by the sampling means; a transport pipe provided between the weight measuring station and the heat chamber, the pipe having a control valve to control the supply of materials from the hopper; a moisture measuring unit led from the upper part of the heat chamber by a branch pipe having a control valve; a control damper provided under the heat chamber to discharge the materials stored in the heat chamber; an inert gas feeding means having a feed port at the lower part of the heat chamber and having a feed pipe interposed by a control valve to control the introduction of pressurized and dried inert gas into the heat chamber; and an operation unit which receives the measured weight value of materials from the weight measuring unit and the titrated and analyzed value from the moisture measuring unit, thereby the operation unit calculating the moisture content of a sampled fixed amount of materials and displaying and outputting the calculated value, a fixed amount of powdered or granular materials sampled by a material sampling means is supplied into a weight measuring unit in an airtight weight measuring station, the weight therein measured and fed into a heat treatment chamber through a supplementary hopper.

A dried inert gas is introduced into the heat treatment chamber at the same time sampled materials are fed therein, thus the outer air is prevented from entering into the chamber. While materials are heated in the chamber, a control valve of a branch pipe leading to a moisture measuring unit is opened in order to send evaporated moisture in the chamber into the unit together with the inert gas.

The weight of materials before being heated is measured in the weight measuring station and the weight value and the titrated and analyzed value of the moisture measuring unit are sent to an operation unit to calculate the moisture content of the materials, and the obtained value being outputted displayed and.

In the system comprising: a material supply means to supply powdered or granular materials; a material measuring chamber provided with a weight detection sensor, for weighing a fixed amount of materials supplied from the supply means and storing the weighed materials therein; a transport pipe connecting the measuring chamber and the supply means, the pipe having a control valve of which open and close operations are controlled by the sensor and having a vent valve to open to atmosphere; a heat treatment chamber with an airtight heating means having enough capacity to contain all the materials stored in the material measuring chamber, the heat chamber being connected under the measuring chamber through a first control damper; a moisture measuring unit led from the upper part of the heat chamber by a branch pipe having a control valve; a second control damper provided under the heat chamber to discharge the materials stored in the heat chamber; an inert gas feeding means having a feed port at the lower part of the heat chamber and having a feed pipe interposed by a control valve to control the introduction of pressurized and dried inert gas into the heat chamber; a weight measuring unit provided under the second damper; and an operation unit which receives the measured weight value of materials from the weight measuring unit and the titrated and analyzed value from the moisture measuring unit, thereby the operation unit calculating the moisture content of a sampled fixed amount of materials and displaying and outputting the calculated value, a fixed amount of powdered or granular materials supplied by a material supply means are fed into a heat treatment chamber then stored in a material measuring chamber provided with a weight detection sensor.

A dried inert gas is introduced into the heat treatment chamber at the same time the sampled materials are fed into the chamber, whereby entrance of outside air into the chamber can be prevented. While materials are contained in the chamber to be heated, a control valve of a branch pipe leading to a moisture measuring unit is opened so as to supply the moisture evaporated in the chamber into the unit together with the inert gas. In the weight measuring unit the heated materials are weighed and the weight value and the titrated and analyzed value of the moisture measuring unit are sent to an operation unit, wherein the moisture content of the sampled materials is calculated and the value is outputted and displayed.

In the system comprising: a material suction unit having a nozzle constructed such that an injection port of pressurized gas is disposed at the initial end side of a material suction port formed at the lateral leading portion of a transport pipe so as to be opposite to the transporting destination of materials, the nozzle being inserted into a bed of powdered or granular materials to suck the materials; a material measuring chamber connected to the suction unit by a transport pipe line having a control valve, the measuring chamber having a weight detection sensor and a filtering device to separate the materials pneumatically transported by the suction unit from the pressurized gas; a heat treatment chamber with an airtight heating means having enough capacity to contain all the materials stored in the material measuring chamber, the heat chamber being connected under the measuring chamber through a first control damper; a moisture measuring unit led from the upper part of the heat chamber by a branch pipe having a control valve; a second control damper provided under the heat chamber to discharge the materials stored in the heat chamber; an inert gas feeding means having a feed port at the lower part of the heat chamber and having a feed pipe interposed by a control valve to control the introduction of pressurized and dried inert gas into the heat chamber; a weight measuring unit provided under the second damper; and an operation unit which receives the measured weight value of materials from the weight measuring unit and the titrated and analyzed value from the moisture measuring unit, thereby the operation unit calculating the moisture content of a sampled fixed amount of materials and displaying and outputting the calculated value, powdered or granular materials sucked in by inserting a nozzle of a material suction unit into a material bed are sent under pressure into a material measuring chamber provided with a weight detection sensor together with an inert gas injected from the nozzle and stored in the measuring chamber after being separated from the gas by a filtering device. The supplying amount of materials is controlled by interlocking the detecting operation of the weight sensor with a control valve. When the sensor detects the storage of a fixed amount of materials, material supply is stopped. Then, the sampled materials are fed into the heat treatment chamber and simultaneously a dried inert gas is introduced therein, thus entrance of outside air therein can be prevented.

While materials are contained in the chamber to be heated, a control valve of a branch pipe leading to a moisture measuring unit is opened so as to supply the moisture evaporated in the chamber into the unit together with the inert gas. In the weight measuring unit the heated materials are weighed and the weight value and the titrated and analyzed value of the moisture measuring unit are sent to an operation unit, wherein the moisture content of the sampled materials is calculated and the value is outputted and displayed. According to those embodiments wherein a material storing chamber to store heated powdered or granular materials is further provided under a heat treatment chamber, an inert gas is introduced from a feed port provided at the lower part of storing chamber. Therefore, in addition to a normal natural heat transfer, the retained heat of materials stored in the storing chamber is transferred into the materials contained in the heat treatment chamber using the inert gas as a medium, whereby an energy-saving system can be achieved by utilizing the retained heat.

In the systems wherein a gas introduction port having breathable material is provided with the control damper instead of providing the inert gas feeding means, the port being connected with a feed pipe leading from an insert gas source through a control valve to control the supply of pressurized and dried inert gas, a control damper provided under a heat treatment chamber or a material storing chamber can introduce the inert gas when the damper is closed, whereby a feed port to introduce the inert gas at the lower part of heat chamber or storing chamber isn't required and the construction of the system can be simplified.

In the system wherein a weight detection sensor is provided for the material storing chamber, the discharge of one sample of powdered or granular materials stored in a material storing chamber can be facilitated by controlling opening and closing operations of a control damper by the detection of the sensor.

In the system wherein, the value analyzed and titrated and the apparent specific weight and the volume of sampled materials are input into an operation unit, the moisture content is calculated by the operation unit instead of by the weight measuring unit.

As is apparent from the above-mentioned explanations, the following effects can be obtained by the present invention.

According to the on-line moisture control method of the present invention, powdered or granular materials are sampled automatically several times at fixed intervals, transported into a dried heat treatment chamber, heated therein and titrated and analyzed by a moisture measuring unit, whereby a moisture control of materials which has been conventionally conducted by inspector's hands in a laboratory can be executed on-line, easily and quickly. Consequently, a moisture control of materials before they are heated and after they are heated which have been considered to be difficult can be carried out easily and precisely.

According to several of the on-line moisture control systems noted above, the inert gas is introduced into the heat treatment chamber at the same time powdered or granular materials are supplied in the chamber by the use of a mechanical material transporting means, whereby enterance of outside air into the chamber is prevented. As sampled materials are heated in the chamber and the moisture evaporated at this time is sent to a moisture measuring unit together with the inert gas, the moisture can be easily titrated and analyzed. Further, as the weight of materials before they are heated or after they are heated is simultaneously measured when materials are fed into the system and as the weight value and the analyzed value are input into an operation unit and the result is displayed and output, a series of operations from the automatic sampling of materials to the measurement of moisture content can be executed on-line, simply and quickly.

Further according to one of the noted systems of the present invention, powdered or granular materials are pneumatically transported by inserting a material suction unit having a nozzle constructed such that an injection port of pressurized gas is disposed at the initial end side of a material suction port formed at the lateral leading portion of the pipe so as to be opposite to the transporting destination of the materials. Therefore, materials can be transported under pressure in a thin pipe without causing clogging and the transportation of a small amount of materials by a pipe of small caliber can be achieved. Consequently, an on-line moisture control system which is preferably used in a molding site where a small amount and many kinds of resin materials are exchanged frequently can be realized.

Furthermore according to one of the noted systems of the present invention, as the retained heat of heated powdered or granular materials stored in a material storing chamber provided under a heat treatment chamber can be utilized, an on-line moisture control system characterized by quickness and energy saving in addition to the above-mentioned effects can be fulfilled.

Especially according to the system of the present invention wherein a gas introduction port having breathable material is provided with the control damper instead of providing the inert gas feeding means, the port being connected with a feed pipe leading from an inert gas source through a control valve to control the supply of pressurized and dried inert gas, an on-line moisture control system which has a heat treatment chamber of simplified design and a material storing chamber is realized by removing a feed port to introduce an inert gas at the lower part of these chambers.

Especially according to the system of the present invention wherein the apparent specific weight of sampled materials and the volume of sampled materials are input into the operation unit instead of providing a material measuring unit, an on-line moisture control system of simplified construction is fulfilled by removing a weight measuring unit.

It is further understood by those skilled in the art that the foregoing description is a preferred embodiment of the present invention and that various changes and modifications may be made in the invention without departing from the spirit and scope thereof.

What is claimed is:

1. An on-line moisture control system for powdered materials, comprising:

material sampling means having a measuring device to sample a fixed amount of powdered materials;

a heat treatment chamber with an airtight heating means having a capacity sufficient to contain the materials sampled by said material sampling means;

a transport pipe provided between said material sampling means and said heat treatment chamber, said transport pipe having a control valve to control the supply of materials from said material sampling means and having a gas vent valve to open to atmosphere;

a moisture measuring unit led from the upper part of said heat treatment chamber by a branch pipe having a control valve, for providing a titrated and analyzed value;

a control damper provided under said heat treatment chamber to discharge the materials stored in said heat treatment chamber;

inert gas feeding means comprising a feed port at the lower part of said heat treatment chamber and a feed pipe interposed by a control valve to control the introduction of pressurized and dried inert gas into said heat treatment chamber;

a weight measuring unit provided under said control damper, for providing a measured weight value of the powdered material; and a operation unit which receives the measured weight value of materials from said weight measuring unit and the titrated and analyzed value from said moisture measuring unit, and calculates the moisture content of a sampled fixed amount of materials, and displays and outputs the calculated value.

2. An on-line moisture control system for powdered materials as set forth in claim 4, wherein the sampled materials have an apparent specific weight and a volume, and wherein the apparent specific weight of sampled materials and the volume of sampled materials are input into said operation unit.

* * * * *

UNITED STATES PATENT AND TRADEMARK OFFICE
CERTIFICATE OF CORRECTION

PATENT NO. : 5,274,931
DATED : January 4, 1994
INVENTOR(S) : Hiroshi Ogiri et al It is certified that error appears in the above-identified patent and that said Letters Patent is hereby corrected as shown below:

Claim 1, column 18, line 14, "a" should be "an".

Signed and Sealed this

Fourteenth Day of June, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,274,931

DATED : January 4, 1994

INVENTOR(S) : Hiroshi Ogiri et al

It is certified that error appears in the above-identified patent and that said Letters Patent is hereby corrected as shown below:

Claim 2, column 18, line 21, "4" should be "1".

Signed and Sealed this

Twelfth Day of July, 1994

*Attest:*

BRUCE LEHMAN

*Attesting Officer*     *Commissioner of Patents and Trademarks*